US008022104B2

(12) United States Patent
Licht et al.

(10) Patent No.: US 8,022,104 B2
(45) Date of Patent: Sep. 20, 2011

(54) FORMULATIONS OF LADOSTIGIL TARTRATE

(75) Inventors: Daniella Licht, Kiriat-Ono (IL); Ioana Lovinger, Kfar-Saba (IL); Fanny Caciularu, Petach Tikva (IL); Adrian Gilbert, Ra'nanna (IL)

(73) Assignees: Yissum Research Development Company of the Hebrew University of Jerusalem, Jerusalem (IL), part interest; Technion Research and Development Foundation Ltd., Haifa (IL), part interest ( * ) Notice: Subject to any disclaimer, the term of this patent is extended or adjusted under 35 U.S.C. 154(b) by 542 days.

(21) Appl. No.: 11/361,379

(22) Filed: Feb. 24, 2006

(65) Prior Publication Data
US 2006/0189685 A1 Aug. 24, 2006

Related U.S. Application Data

(60) Provisional application No. 60/656,477, filed on Feb. 24, 2005.

(51) Int. Cl.
*A61K 31/27* (2006.01)
*A61K 31/21* (2006.01)
*A61K 31/135* (2006.01)
(52) U.S. Cl. .......................... 514/480; 514/510; 514/656
(58) Field of Classification Search .................. 514/480, 514/510, 656
See application file for complete search history.

(56) References Cited

U.S. PATENT DOCUMENTS

| 3,903,297 | A | 9/1975 | Robert | 424/305 |
|---|---|---|---|---|
| 5,532,415 | A | 7/1996 | Youdim | 564/308 |
| 6,251,938 | B1 | 6/2001 | Chorev | 560/136 |
| 6,303,650 | B1 | 10/2001 | Chorev et al. | 435/136 |
| 6,316,504 | B1 | 11/2001 | Youdim et al. | |
| 6,462,222 | B1 | 10/2002 | Chorev | 560/28 |
| 6,538,025 | B2 | 3/2003 | Chorev | 514/480 |
| RE39,616 | E | 5/2007 | Chorev | 514/480 |
| 2004/0010038 | A1 | 1/2004 | Blaugrund | 562/27 |
| 2005/0065176 | A1* | 3/2005 | Field et al. | |
| 2005/0267077 | A1 | 12/2005 | Gallagher | 514/750 |
| 2006/0189685 | A1 | 8/2006 | Licht | 514/183 |
| 2006/0189819 | A1 | 8/2006 | Bahar | |
| 2006/0276537 | A1 | 12/2006 | Goren et al. | |
| 2007/0135518 | A1 | 6/2007 | Weinstock-Rosin | |
| 2007/0203232 | A1 | 8/2007 | Piryatinsky | |
| 2007/0232691 | A1 | 10/2007 | Goren | 514/484 |
| 2009/0131535 | A1 | 5/2009 | Blaugrund | 514/657 |
| 2010/0093848 | A1 | 4/2010 | Piryatinsky | 562/41 |

FOREIGN PATENT DOCUMENTS

| EP | 0951284 | 10/2003 |
|---|---|---|
| EP | 0951285 | 10/2003 |
| WO | WO9518617 | 7/1995 |
| WO | WO 98/26775 | 6/1998 |
| WO | WO 98/27055 | 6/1998 |
| WO | WO 03/072055 | 9/2003 |
| WO | WO 2005/051371 | 6/2005 |
| WO | WO 2006/091656 | 8/2006 |
| WO | WO 2006/091836 | 8/2006 |
| WO | WO 2006/130726 | 12/2006 |
| WO | WO 2007/070425 | 6/2007 |
| WO | WO 2007/087029 | 8/2007 |
| WO | WO 2007/100583 | 9/2007 |

OTHER PUBLICATIONS

"USP and NF Excipients", The United States Pharmacopeia and The National Formulary, 2004, pp. 2809-2812.*
Parikh, "Granulation Growth Mechanisms and Granulation Characteristics", Handbook of Pharmaceutical Granulation Technology, 1997, pp. 160-165.*
Mealy et al., (2004)"Ladostigil Hemitartrate", Drugs of the Future, Abstract 2004176769 29(3) :293.
Youdim et al., (2005) "Rasagiline Neurodegeneration, Neuroprotection, and Mitochondrial Permeability Transition" Journal of Neuroscience Research, 79:172-179.
CAS Abstract Service registry No. 209394-46-7 (1998) 1 page.
Sterling et al., (2002) Journal of Medicinal Chemistry 45:5260-5279.
U.S. Appl. No. 60/656,866, filed Feb. 24, 2005, Bahar, Eliezer.
U.S. Appl. No. 60/686,791, filed Jan. 1, 2005, Goren, Tamar.
U.S. Appl. No. 60/700,850, filed Jul. 19, 2005, Goren, Tamar.
U.S. Appl. No. 11/091,008, filed Mar. 25, 2005, Chorev, Michael.
U.S. Appl. No. 11/637,600, filed Dec. 11, 2006, Weinstock, Eran.
ISR of PCT/US2006/006636 Aug. 28, 2007.
U.S. Appl. No. 11/635,922 Final Rejection Jun. 8, 2010.
U.S. Appl. No. 11/637,600 Non-Final Rejection Jun. 9, 2010.
Tyurin, V. A. et al., (2000) Oxidative stress following traumatic brain injury in rats: Quantitation of biomarkers and detection of free radical intermediates. Journal of Neurochemistry 75(5):2178-2189.
Handbook of Pharmaceutical Excipients. Published by the Pharmaceutical Press and the American Pharmacist Association. Fourth edition (2003). Edited by ROWE, Raymond C. et al., pp. 188, 430, 449, 705, 725-726, 737-738, 767.
Chen, Yun et al., (1998) Cerebro-protective effects of ENA713, a novel acetylcholinesterase inhibitor, in closed head injury in the rat. Brain Research 784:18-24.
Chen, Yun et al., (1998) Rivastigmine, a brain-selective acetylcholinesterase inhibitor, ameliorates congnitive and motor deficits induced by closed-head injury in the mouse. Journal of Neurotrauma 15(4):231-237.
Feldman, Howard H. et al., (2007) Effect of rivastigmine on delay to diagnosis of Alzheimer's disease from mild cognitive impairment: the InDDEx study. Lancet Neurology 6(6):501-512.
Moreira, P. I. et al., (2005) Oxidative stress mechanisms and potential therapeutics in Alzheimer disease. Journal of Neural transmission 112(7):921-932.
Physician's Desk Reference (2005) 59th edition Publisher: Charles E. Baker, Jr. pp. 1583-1585.
Rosen, Wilma G. et al., (1984) A new rating scale for Alzheimer's disease. Am J Psychiatry 141:1356-1364.
Rubin, Harold (2009) Mild Cognitive Impairment-Alzheimer's Disease Part XVI e-published on www.therubins.com June 14, 2009, 8 pages.

(Continued)

Primary Examiner — James Anderson
Assistant Examiner — Gregg Polansky
(74) Attorney, Agent, or Firm — Winston & Strawn LLP

(57) ABSTRACT

Disclosed are formulations of ladostigil tartrate, including pharmaceutical compositions, process for the manufacture, and use thereof.

11 Claims, No Drawings

OTHER PUBLICATIONS

Weinstock, M. et al., (2005) Ladostigil attenuates gliosis and prevents oxidative-nitrative stress in hippocampus and memory deficits induced in rats by intracerebroventricular injection of streptozotocin. Reviews in the Neurosciences, Tel-Aviv, Israel16(suppl):S67.

Weinstock, M. and Shoham, S. (2004) Rat models of dementia based on reductions in regional glucose metabolism, cerebral blood flow and cytochrome oxidase activity. J Neural Trans. 111(3):347-366.

U.S. Appl. No. 11/635,922 Requirement for restriction/election May 13, 2009.

U.S. Appl. No. 11/635,922 Non-final rejection Oct. 15, 2009.

U.S. Appl. No. 11/635,922 Final rejection Jun. 8, 2010.

U.S. Appl. No. 11/637,600 Requirement for restriction/election May 7, 2009.

U.S. Appl. No. 11/637,600 Non-final rejection Oct. 15, 2009.

U.S. Appl. No. 11/637,600 Non-final rejection Jun. 9, 2010.

Arnaiz, E. et al., (2001) Impaired cerebral glucose metabolism and cognitive functioning predict deterioration in mild cognitive impairment. Neuroreport 12(4):851-5.

Bartolini, L. et al., (1996) Aniracetam restores object recognition impaired by age, scopolamine, and nucleus basalis lesions. Pharmacol Biochem Behav. 53(2):277-83.

Bolanos, Juan P. et al., (2004) Regulation of glucose metabolism by nitrosative stress in neural cells. Mol Aspects Med. 25(1-2):61-73.

Buccafusco, J. J. et al., (2003) Potential Cognitive actions of (N-Propargly -(3 R)-aminoindan-5-yl)-ethyl, methyl carbamate (TV3326), a novel neuroprotective agent, as assessed in old Rhesus monkeys in their performance of versions of a delayed matching task. Neuroscience 119:669-678.

Casu, Maria Antonietta et al., (2002) Aging causes a preferential loss of cholinergic innervation of characterized neocortical pyramidal neurons. Cereb Cortex 12(3):329-337.

Ellman, George L. et al., (1961) A new and rapid colorimetric determination of acetylcholinesterase activity. Biochem. Pharmacol. 7(2):88-95.

Finch, Caleb E. (2003) Neurons, glia, and plasticity in normal brain aging. Neurobiol. Aging 24:S123-7.

Good, Paul F. et al., (1996) Evidence of neuronal oxidative damage in Alzheimer's disease. Am J Pathol. 149(1):21-8.

Gordon, Christopher J. (1994) Thermoregulation in laboratory mammals and humans exposed to anti-cholinesterase agents. Neurotoxicol. Teratol. 16(5):427-453.

Griffin, W. S. T. et al., (1998) Glial-neuronal interactions in Alzheimer's disease: the potential role of a 'cytokine cycle' in disease progression. Brain Pathol. 8(1):65-72.

Hensley, K. et al., in "Neuroinflammation: mechanisms and management" (Ed: P. L. Wood), Humana Press Inc., 1997, pp. 265-281.

Intelihealth, "Alzheimer's disease," online accessed Jun. 30, 2008, http://www.intelihealth.com/IH/intlh/WSIHW000/8303/9117/195703.html?d=dmtHealthAZ.

Intelihealth, "Dementia," online, accessed Sep. 22, 2009, http://www.intelihealth.com/IH/intlh/WSIHW000/24479/11184.html.

Intelihealth, "Parkinson's disease," online accessed Sep. 22, 2009, http://www.intelihealth.com/IH/intIH?d=dmtHealthAZ&c=201957.

Kielian, Tammy and Esen, Nilufer (2004) Effects of neuroinflammation on glia-glia gap junctional intercellular communication: a perspective. Neurochem Int. 45(2-3):429-36.

Lannert, Heinrich and Hoyer, Siegfried (1998) Intracerebroventricular administration of streptozotocin causes long-term diminutions in learning and memory abilities and in cerebral energy metabolism in adult rats. Behav Neurosci.112(5):1199-1208.

Lipton, Stuart A. and Rosenbrg, Paul A.(1994) Excitatory amino acids as a final common pathway for neurological disorders N Engl J Med. 330(9):613-22.

Maruyama, Wakako et al., (2003) Anti-apoptotic action of anti-Alzheimer drug, TV3326 [(N-propargyl)-(3R)-aminoindant-5-yl]-ethyl methyl carbamate, a novel cholinesterase-monoamine oxidase inhibitor. Neurosci Lett. 341(3):233-236.

Mattson, Mark P. et al., (1997) Activation of NF-KB protects hippocampal neurons against oxidative stress-induced apoptosis: Evidence for induction of manganese superoxide dismutase and suppression of peroxynitrite production and protein tyrosine nitration. J Neurosci Res. 49(6):681-697.

McCarty, Mark F. (2006) Down-regulation of microglial activation may represent a practical strategy for combating neurodegenerative disorders. Med Hypotheses 67(2):251-269.

McGeer, Edith G. and McGeer, Patick L. (2003) Inflammatory processes in Alzheimer's disease. Prog. Neuro-Psychopharmacol. Biol. Psychiatry 27(5):741-9.

Meyer, John Stirling et al., (2005) MRI Abnormalities Associated with Mild Cognitive Impairments of Vascular (VMCI) Versus Neurodegenerative (NMCI) Types Prodromal for Vascular and Alzheimer's Dementias. Curr Alz Res 2(5):579-585.

Miguel-Hidalgo, J. J. et al., (2002) Neuroprotection by memantine against neurodegeneration induced by beta-amyloid (1-40), Brain Res. 958(1):210-221.

Moriera, P. I. et al., (2005) Oxidative stress mechanisms and potential therapeutics in Alzheimer disease. J Neural Transmission 112(7):921-932.

Mumby, Dave G. et al., (2002) Hippocampal damage and exploratory preferences in rats: memory for objects, places, and contexts. Learn Mem. 9(2):49-57.

Nitch, R. et al., (1989) The intracerebroventricularly streptozotocin-treated rat: impairment of cerebral glucose metabolism resembles the alterations of carbohydrate metabolism of the brain in Alzheimer's disease, J. Neural Transm. P-D sect 1(1-2):109-10.

Ouyang, Yi-Bing and Giffard, Rona G. (2004) Changes in astrocyte mitochondrial function with stress: effects of Bcl-2 family proteins. Neurochem Int. 45(2-3):371-9.

Petersen, Ronald C. et al., (2001) Current concepts in mild cognitive impairment. Arch Neurol. 58(12):1985-92.

Poltyrev, Tatyana et al., (2005) Effect of chronic treatment with ladostigil (TV-3326) on anxiogenic and depressive-like behaviour and on activity of the hypothalamic-pituitary-adrenal axis in male and female prenatally stressed rats. Psychopharmacology (Berl) 181(1):118-25 Epub Oct 15, 2005.

Sagi, Yotam et al., (2003) Attenuation of MPTP-induced dopaminergic neurotoxicity by TV3326, a cholinesterase-monoamine oxidase inhibitor. J Neurochem. 86:290-297.

Sagi, Yotam et al., (2005) The neurochemical and behavioural effects of the novel cholinesterase-monoamine oxidase inhibitor, ladostigil, in response to L-dopa and L-tryptophan, in rats. Br J Pharmacol. 146(4):553-60.

Scali, C. et al., (2002) Effect of subchronic administration of metrifonate, rivastigmine and donepezil on brain acetylcholine in aged F344 rats. J. Neural Transm. 109(7-8):1067-1080.

Sharma, Monisha and Gupta, Y. K. (2001) Effect of chronic treatment of melatonin on learning, memory and oxidative deficiencies induced by intracerebroventricular streptozotocin in rats. Pharmacol Biochem Behav 70(2-3):325-331.

Sharma, Monish and Gupta, Y. K. (2002) Chronic treatment with trans resveratrol prevents intracerebroventricular streptozotocin induced cognitive impairment and oxidative stress in rats. Life Sci 71(21):2489-2498.

Shoham, S. et al., (2003) Intracerebroventricular injection of streptozotocin causes neurotoxicity to myelin that contributes to spatial memory deficits in rats. Exp Neural. 184(2):1043-52.

Shoham, Shai et al., (2007) Ladostigil prevents gliosis, oxidative-nitrative stress and memory deficits induced by intracerebroventricular injection of streptozotocin in rats. Neuropharmacol 52(3):836-843.

Shytle, R. Douglas et al., (2004) Cholinergic modulation of microglial activation by alpha 7 nicotinic receptors. J Neurochem. 89(2):337-43.

Simmons, Martha L. and Murphy, Sean (1992) Induction of nitric oxide synthase in glial cells. J Neurochem. 59(3):897-905.

Takasu, N. et al., (1991) Streptozocin- and alloxan-induced $H_2O_2$ generation and DNA fragmentation in pancreatic islets. $H_2O_2$ as mediator for DNA fragmentation. Diabetes. 40(9):1141-5.

Takuma, Kazuhiro et al., (2004) Astrocyte apoptosis: implications for neuroprotection. Prog Neurobiol. 72(2):111-127.

Turrini, P. et al., (2001) Cholinergic nerve terminals establish classical synapses in the rat cerebral cortex: synaptic pattern and age-related atrophy. Neurosci. 105(2):277-285.

Wahlgren, N. G. in R. Green, "International Review of Neurobiology: Neuroprotective Agents and Cerebral Ischemia", vol. 40, Academic Press, 1997, pp. 337-363.

Wang, R. H. et al., (2000) Gender differences in the effect of rivastigmine on brain cholinesterase activity and cognitive function in rats. Neuropharmacology 39(3):497-506.

Weinstock, M. et al., (2000) TV3326, a novel neuroprotective drug with cholinesterase and monoamine oxidase inhibitory activities for the treatment of Alzheimer's disease. J Neural Transm. Suppl. 60:157-69.

Weinstock, M. et al., (2000) Development of a novel neuroprotective drug (TV3326) for the treatment of Alzheimer's disease, with cholinesterase and monoamine oxidase inhibitory activities. Drug Dev. Res. 50: 216-222.

Weinstock, Marta et al., (2001) Neuroprotective Effects of Novel Cholinesterase Inhibitors Derived from Rasagiline as Potential Anti-Alzheimer Drugs. Ann. N.Y. Acad. Sci. 939:148-161.

Weinstock, M. et al., (2002) Limited potentiation of blood pressure response to oral tyramine by brain-selective monoamine oxidase A-B inhibitor, TV-3326 in conscious rabbits. Neuropharmacology 43(6):999-1005.

Weinstock, Marta et al., (2002) Effect of TV3326, a novel monoamine-oxidase cholinesterase inhibitor, in rat models of anxiety and depression, Psychopharmacology. 160(3):318-24.

Weinstock, M. et al., (2003) A novel cholinesterase and brain-selective monoamine oxidase inhibitor for the treatment of dementia co-morbid with depression and Parkinson's disease. Prog. Neuropsychopharmacol. Biol. Psychiatry 27: 555-561.

Winters, et al., Double dissociation between the effects of peri-postrhinal cortex and hippocampal lesions on tests of object recognition and spatial memory: heterogeneity of function within the temporal lobe, J. Neuroscience (2004) 24:5901-8.

Yogev-Falach, Merav et al., (2002) Involvement of MAP kinase in the regulation of amyloid precursor protein processing by novel cholinesterase inhibitors derived from rasagiline. FASEB 16:1674-1676.

Yogev-Falach, Merav et al., (2006) A multifunctional, neuroprotective drug, ladostigil (TV3326), regulates holo-APP translation and processing. FASEB 20:E1610-E1618.

Youdim, Moussa B. H. and Weinstock, Marta (2001) Molecular Basis of Neuroprotective Activities of Rasagiline and the Anti-Alzheimer Drug TV3326 [Ipar;N-Propargyl-(3R) Aminoindan-5-YL)-Ethyl Methyl Carbamate] Cell Mol Neurobiol. 21(6):555-73.

Youdim, Moussa B. H. and Weinstock, Marta (2002) Novel neuroprotective anti-Alzheimer drugs with anti-depressant activity derived from the anti-Parkinson drug, rasagiline. Mechanisms of Ageing and Development 123 (2002) 1081-1086.

Youdim, Moussa B. H. et al., (2003) Amyloid processing and signal transduction properties of antiparkinson—antialzheimer neuroprotective drugs Rasagiline and TV3326. Ann. N.Y. Acad Sci 993:378-386.

Youdim, Moussa B. H. and Weinstock, Marta (2004) Therapeutic applications of selective and non-selective inhibitors of monoamine oxidase A and B that do not cause significant Tyramine potentiation. Neurotoxicology 25:243-250.

Chemical Abstract Service, (Columbus Ohio), Registry No. 209394-46-7, Aug. 4, 1998.

Guidance for Industry: Estimating the Maximum Safe Starting Dose in Initial Clinical Trials for Therapeutics in Adult Healthy Volunteers, U.S. Dept. HHS/FDA/CDER (Jul. 2005), at http://www.fda.gov/cder/guidance/5541fnl.doc, pp. 1-27.

U.S. Appl. No. 11/637,600 Requirement for restriction election dated May 7, 2009.

U.S. Appl. No. 11/637,600 Non-Final Rejection dated Oct. 15, 2009.

International Search Report of PCT/US2006/047038 mailed Dec. 11, 2007.

International Preliminary Examination Report of PCT/US2006/047038 mailed Dec. 11, 2007.

* cited by examiner

FORMULATIONS OF LADOSTIGIL TARTRATE

This application claims the benefit of U.S. Provisional Application No. 60/656,477, filed Feb. 24, 2005, the entire contents of which are hereby incorporated by reference.

Throughout this application various publications, published patent applications, and published patents are referenced. The disclosures of these publications in their entireties are hereby incorporated by reference into this application in order to more fully describe the state of the art to which this invention pertains.

FIELD OF THE INVENTION

The present invention relates to formulations of tartrate salt of R(+)-6-(N-methyl, N-ethyl-carbamoyloxy)-N'-propargyl-1-aminoindan.

BACKGROUND OF THE INVENTION

PCT Application Publication No. WO98/27055 discloses indanylamine and aminotetralin derivative compounds, such as those of Formula I below, which are useful to treat depression, Attention Deficit Disorder (ADD), Attention Deficit and Hyperactivity Disorder (ADHD), Tourette's Syndrome, Alzheimer's Disease and other dementias. The indanylamine derivatives disclosed have been show to have biological effects in animal models of neurological disease. In addition, PCT Application Publication No. WO98/27055 discloses methods for preparation of the indanylamine derivative compounds.

Formula I:

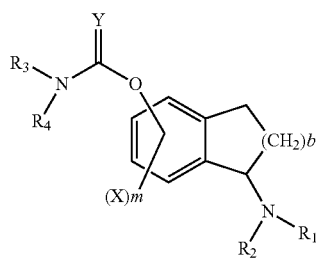

wherein b is 1 or 2; m is 0-3; Y is O or S; X is halo; $R_1$ is hydrogen or $C_{1-4}$ alkyl; $R_2$ is hydrogen, $C_{1-4}$ alkyl, or optionally substituted propargyl; and $R_3$ and $R_4$ are each independently hydrogen, $C_{1-8}$ alkyl, $C_{6-12}$ aryl, $C_{6-12}$ aralkyl, each optionally halo substituted.

R(+)-6-(N-methyl, N-ethyl-carbamoyloxy)-N'-propargyl-1-aminoindan, also known as (3R)-3-(prop-2-ynylamino)-2,3,-dihydro-1H-inden-5-yl ethylmethylcarbamate, is disclosed in PCT Application Publication No. WO98/27055, specifically compound 76 in Table 5. In addition, salts are disclosed, including the ½ L-tartrate salt. This salt has been given the nonproprietary name ladostigil tartrate. Its CAS registry number is 209394-46-7.

Specific pharmaceutical compositions, i.e., formulations, comprising ladostigil tartrate suited for storage and desired pharmacokinetics have not been previously disclosed.

SUMMARY OF THE INVENTION

The subject invention provides a formulation comprising tartrate salt crystals of R(+)-6-(N-methyl, N-ethyl-carbamoyloxy)-N'-propargyl-1-aminoindan.

The subject invention also provides a pharmaceutical composition comprising R(+)-6-(N-methyl, N-ethyl-carbamoyloxy)-N'-propargyl-1-aminoindan ½ tartrate, at least one pharmaceutically acceptable excipient and up to 5% by weight of the composition of water.

The subject invention also provides a pharmaceutical composition comprising R(+)-6-(N-methyl, N-ethyl-carbamoyloxy)-N'-propargyl-1-aminoindan ½ tartrate, at least one pharmaceutically acceptable excipient and no more than 0.5% by weight of the composition of magnesium stearate.

The subject invention also provides a pharmaceutical composition comprising R(+)-6-(N-methyl, N-ethyl-carbamoyloxy)-N'-propargyl-1-aminoindan ½ tartrate, at least one pharmaceutically acceptable excipient and no more than 1.5% by weight of the composition of sodium stearyl fumarate.

The subject invention also provides a pharmaceutical composition comprising R(+)-6-(N-methyl, N-ethyl-carbamoyloxy)-N'-propargyl-1-aminoindan ½ tartrate and a pharmaceutically acceptable carrier, formulated so as to provide upon administration to a human subject a maximum blood plasma concentration of R(+)-6-(N-methyl, N-ethyl-carbamoyloxy)-N'-propargyl-1-aminoindan of at least 0.7 nmol/mL.

The subject invention also provides a method for inducing in a human subject a maximum blood plasma concentration of R(+)-6-(N-methyl, N-ethyl-carbamoyloxy)-N'-propargyl-1-aminoindan of at least 0.7 nmol/mL after one administration, comprising administering orally to the human subject a solid pharmaceutical composition comprising R(+)-6-(N-methyl, N-ethyl-carbamoyloxy)-N'-propargyl-1-aminoindan ½ tartrate and a pharmaceutically acceptable carrier so as to induce in the subject the blood plasma concentration.

DETAILED DESCRIPTION OF THE INVENTION

The subject invention provides a pharmaceutical composition comprising R(+)-6-(N-methyl, N-ethyl-carbamoyloxy)-N'-propargyl-1-aminoindan ½ tartrate, at least one pharmaceutically acceptable excipient and up to 5% by weight of the composition of water.

In an embodiment, the pharmaceutical composition comprises 2-5% water.

In a further embodiment, the pharmaceutical composition comprises 1-5% water.

In a further embodiment, the pharmaceutical composition comprises 1.5-4% water.

In yet a further embodiment, the pharmaceutical composition comprises 2-3.5% water.

In yet a further embodiment, the pharmaceutical composition comprises 2-3.5% water.

The subject invention also provides a pharmaceutical composition comprising R(+)-6-(N-methyl, N-ethyl-carbamoyloxy)-N'-propargyl-1-aminoindan ½ tartrate, at least one pharmaceutically acceptable excipient and no more than 0.5% by weight of the composition of magnesium stearate.

In an embodiment, the pharmaceutical composition is free of magnesium stearate.

The subject invention also provides a pharmaceutical composition comprising R(+)-6-(N-methyl, N-ethyl-carbamoyloxy)-N'-propargyl-1-aminoindan ½ tartrate, at least one pharmaceutically acceptable excipient and no more than 1.5% by weight of the composition of sodium stearyl fumarate.

In an embodiment, the composition comprises no more than 0.5% by weight of the composition of sodium stearyl fumarate.

In another embodiment, the pharmaceutical composition is free of sodium stearyl fumarate.

In another embodiment, no more than 0.5% by weight of the composition is magnesium stearate.

In another embodiment, the pharmaceutical composition is free of magnesium stearate and of stearic acid.

In another embodiment, no more than 0.5% by weight of the composition is sodium stearyl fumarate.

In another embodiment, the pharmaceutical composition is free of sodium stearyl fumarate.

In another embodiment, no more than 0.5% by weight of the composition is stearic acid.

In another embodiment, the pharmaceutical composition is free of stearic acid.

In yet another embodiment, at least one pharmaceutically acceptable excipient is a first filler, a second filler, a disintegrant, a flow agent, a binder and a lubricant.

In yet another embodiment, the lubricant is talc.

In yet another embodiment, talc is present in an amount of up to 4% by weight of the composition.

In yet another embodiment, the lubricant further comprises stearic acid.

In yet another embodiment, the stearic acid is present in an amount of up to 2% by weight of the composition.

In yet another embodiment, the lubricant is stearic acid.

In yet another embodiment, the pharmaceutical composition is free of talc.

In yet another embodiment, the pharmaceutical composition is free of stearic acid.

In a further embodiment, the first filler is mannitol present in an amount of 6 to 16% by weight, the second filler is mannitol granulate present in an amount of 0 to 56% by weight, the disintegrant is starch present in an amount of 15 to 38% by weight, the flow agent is colloidal silicon dioxide present in an amount of 1 to 2% by weight, and the binder is polyvinylpyrrolidone present in an amount of 3 to 8% by weight.

In yet a further embodiment, the first filler is mannitol present in an amount of 6.6% by weight, the second filler is mannitol granulate present in an amount of 56.1% by weight, the disintegrant is starch present in an amount of 15.2% by weight, the flow agent is colloidal silicon dioxide present in an amount of 0.9% by weight, the binder is polyvinylpyrrolidone present in an amount of 3.4% by weight, and the lubricant is talc in an amount of 3.8% by weight and stearic acid in an amount of 1.9% by weight.

In yet a further embodiment, the first filler is mannitol present in an amount of 16.4% by weight, the disintegrant is starch present in an amount of 37.5% by weight, the flow agent is colloidal silicon dioxide present in an amount of 2.1% by weight, the binder is polyvinylpyrrolidone present in an amount of 8.4% by weight, and the lubricant is talc in an amount of 3.7% by weight and stearic acid in an amount of 1.9% by weight.

In yet a further embodiment, the pharmaceutical is in the form of tablets, capsules, pills, powders, or granules.

In yet a further embodiment, the pharmaceutical composition is in tablet form.

In yet a further embodiment, the pharmaceutical composition is in capsule form.

In yet a further embodiment, the pharmaceutical composition upon administration to a human subject provides a maximum blood plasma concentration of R(+)-6-(N-methyl, N-ethyl-carbamoyloxy)-N'-propargyl-1-aminoindan of at least 0.7 nmol/mL.

The subject invention also provides a pharmaceutical composition comprising R(+)-6-(N-methyl, N-ethyl-carbamoyloxy)-N'-propargyl-1-aminoindan 2 tartrate and a pharmaceutically acceptable carrier, formulated so as to provide upon administration to a human subject a maximum blood plasma concentration of R(+)-6-(N-methyl, N-ethyl-carbamoyloxy)-N'-propargyl-1-aminoindan of at least 0.7 nmol/mL.

In an embodiment, the pharmaceutical composition is formulated so as to provide in the human subject a blood plasma concentration of R(+)-6-(N-methyl, N-ethyl-carbamoyloxy)-N'-propargyl-1-aminoindan of at least 0.01 nmol/mL twelve hours after dosing.

In another embodiment, the pharmaceutical composition is formulated so as to provide in the human subject a blood plasma concentration of R(+)-6-(N-methyl, N-ethyl-carbamoyloxy)-N'-propargyl-1-aminoindan of at least 1.88 nmol/mL.

In another embodiment, the pharmaceutical composition is formulated so as to provide a monoamine oxidase B inhibition of 59%-91% upon administration to a human subject as determined by liquid scintillation counting.

In yet another embodiment, the pharmaceutical composition is formulated so as to provide a monoamine oxidase B inhibition of 75% upon administration to a human subject as determined by liquid scintillation counting.

In a further embodiment, the pharmaceutical composition is formulated so as to provide a 28%-86% decrease of 3,4-dihydroxyphenylglycol plasma concentration upon administration to a human subject as determined by liquid scintillation counting.

In a further embodiment, the pharmaceutical composition is formulated so as to provide a 57% decrease of 3,4-dihydroxyphenylglycol plasma concentration upon administration to a human subject as determined by liquid scintillation counting.

In yet a further embodiment, the pharmaceutical composition administered comprises 25-105 mg R(+)-6-(N-methyl, N-ethyl-carbamoyloxy)-N'-propargyl-1-aminoindan ½ tartrate.

The subject invention also provides a method for inducing in a human subject a maximum blood plasma concentration of R(+)-6-(N-methyl, N-ethyl-carbamoyloxy)-N'-propargyl-1-aminoindan of at least 0.7 nmol/mL after one administration, comprising administering orally to the human subject a solid pharmaceutical composition comprising R(+)-6-(N-methyl, N-ethyl-carbamoyloxy)-N'-propargyl-1-aminoindan ½ tartrate and a pharmaceutically acceptable carrier so as to induce in the subject the blood plasma concentration.

In an embodiment of the method, the blood plasma concentration of R(+)-6-(N-methyl, N-ethyl-carbamoyloxy)-N'-propargyl-1-aminoindan 12 hours after administration is at least 0.01 nmol/mL.

In another embodiment of the method, the maximum blood plasma concentration of R(+)-6-(N-methyl, N-ethyl-carbamoyloxy)-N'-propargyl-1-aminoindan is 1.88 nmol/mL.

In another embodiment of the method, the pharmaceutical composition administered comprises 25-105 mg R(+)-6-(N-methyl, N-ethyl-carbamoyloxy)-N'-propargyl-1-aminoindan ½ tartrate.

The subject invention also provides a method of treating a subject afflicted with Parkinson's disease, Alzheimer's disease or dementia, depression or a neurological disorder comprising administering to the subject the pharmaceutical composition as described herein.

In an embodiment, the subject is afflicted with a neurological disorder and the neurological disorder is epilepsy, narcolepsy, amyotrophic lateral sclerosis ("ALS"), memory disorders, panic, post-traumatic stress disorder ("PTSD"), sexual dysfunction, attention deficit and hyperactivity syndrome ("ADHD"), attention deficit disorder, or Tourette's syndrome.

In another embodiment, the subject is afflicted with dementia and the dementia is static dementia, Alzheimer's-type dementia, senile dementia, presenile dementia, progressive dementia, vascular dementia or Lewy body dementia.

In another embodiment, the subject is afflicted with Alzheimer's disease.

In another embodiment, the subject is afflicted with Parkinson's disease.

The subject invention also provides a process for making the pharmaceutical composition comprising the step of wet granulation. In an embodiment, the process comprises the step of wet granulation in the absence of water addition.

In a further embodiment, the step of wet granulation is performed in the presence of isopropanol.

In yet a further embodiment, the process is performed in the absence of ethanol.

As used herein, a "pharmaceutically acceptable" excipient is one that is suitable for use with humans and/or animals without undue adverse side effects (such as toxicity, irritation, and allergic response) commensurate with a reasonable benefit/risk ratio.

A dosage unit may comprise a single compound or mixtures of compounds thereof. A dosage unit can be prepared for oral dosage forms, such as tablets, capsules, pills, powders, and granules.

The drug substance can be administered in admixture with suitable pharmaceutical diluents, extenders, excipients, or carriers (collectively referred to herein as a pharmaceutically acceptable excipient) suitably selected with respect to the intended form of administration and as consistent with conventional pharmaceutical practices. The unit will be in a form suitable for oral administration. The drug substance can be administered alone but are generally mixed with a pharmaceutically acceptable excipient, and co-administered in the form of a tablet or capsule, liposome, or as an agglomerated powder. Capsule or tablets can be easily formulated and can be made easy to swallow or chew; other solid forms include granules, and bulk powders.

Specific examples of pharmaceutically acceptable excipients that may be used to formulate oral dosage forms of the present invention are described, e.g., in U.S. Pat. No. 3,903, 297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert excipient such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Experimental Details

Ladostigil tartrate can be prepared following the disclosure of PCT International Application Publication No. WO98/27055.

Alternatively, ladostigil tartrate can be prepared as indicated in the following example: In a 250 liter reactor, a solution of R(+)-6-(N-methyl, N-ethyl-carbamoyloxy)-N'-propargyl-1-aminoindan (8.3 kg) in isopropanol (52.4 liters) was heated to 60-65° C. The solution was seeded with 50 g of ladostigil tartrate and a solution of L-tartaric acid (2.4 kg) in isopropanol (38.5 liters) was added dropwise over 2.5-3.5 hours. The mixture was maintained at 60-65° C. for 4-15 hr and was then gradually cooled to 0-5° C. The product was collected in a filter drier and was washed with cold isopropanol (77 liters). The wet material was dried in a filter drier in three stages until moisture content was less than 0.5%. In the first drying stage, the product was dried by static drying for 4 hours at 50-60° C. and under vacuum of less than 50 mbar. In the second drying stage, the product was dried while being stirred for 2 hours at 50-60° C. and under vacuum of less than 50 mbar. In the third drying stage the product was dried while being stirred for 2 hours at 78-82° C. and under vacuum of less than 50 mbar.

This alternative process, which can be performed without the seeding step, is better suited for use in a pilot scale and a production scale than a method that follows PCT Application Publication No. WO98/27055. Ladostigil tartrate prepared using this alternative process results in crystals having bulk density of 0.22-0.29 and tapped density of 0.38-0.54 g/ml.

Regardless of how the crystalline ladostigil tartrate was prepared, initial attempts at formulating ladostigil tartrate encountered problems in terms of flowability and compressibility. As a result, improved formulations of ladostigil tartrate are disclosed.

The first formulations of ladostigil tartrate, prepared by dry granulation, are shown in Table 1:

TABLE 1

| | First Formulations | | | | |
|---|---|---|---|---|---|
| Component | Pseudo-Proportional (mg/tablet) | | | Proportional (mg/tablet) | |
| (mg) | 5 mg | 20 mg | 25 mg | 50 mg | Function |
| Ladostigil Tartrate | 6.4 | 25.68 | 32.0 | 64.0 | Drug Substance |
| Mannitol | 45.6 | 26.4 | 20.0 | 40.0 | Filler |

TABLE 1-continued

First Formulations

| Component (mg) | Pseudo-Proportional (mg/tablet) | | | Proportional (mg/tablet) | Function |
|---|---|---|---|---|---|
| | 5 mg | 20 mg | 25 mg | 50 mg | |
| Pregelatinized Starch (STA-RX 1500) | 40.0 | 40.0 | 40.0 | 80.0 | Disintegrant |
| SYLOID 244 FP | 4.5 | 4.5 | 4.5 | 9.0 | Flowing Agent |
| Stearic Acid | 1.5 | 1.5 | 1.5 | 3.0 | Lubricant |
| Sodium Stearyl Fumarate (PRUV) | 2.0 | 2.0 | 2.0 | 4.0 | Lubricant |
| Total Weight | 100.0 | 100.0 | 100.0 | 200.0 | |

In the pseudo-proportional formulations, the amount of ladostigil tartrate and mannitol remains constant, but the ratio between the two changes; the amount of the other excipients remains constant. The proportional formulation is double the formulation of the 25 mg pseudo-proportional formulation.

These formulations proved to be stable at conditions of 30° C./60% RH and RT/60% RH, but change in tablet color occurred at accelerated conditions, specifically 40° C./75% RH after 1-2 months.

In an attempt to increase stability, tablets were prepared according to the formulations in Table 2:

TABLE 2

Second Formulations

| Excipients (mg) | Formulation | | | |
|---|---|---|---|---|
| | O | P | Q | R |
| Ladostigil Tartrate | 32 | 32 | 32 | 32 |
| Mannitol USP | 42 | 42 | 42 | 20 |
| Starch 1500 | 20 | 20 | 20 | 40 |
| SYLOID 244 (Colloidal Silicon Dioxide) | 2.5 | 2.5 | 2.5 | 4.5 |
| Stearic Acid | 1.5 | 1.5 | 1.5 | 1.5 |
| PRUV (Sodium stearyl fumarate) | 0 | 2.0 | 0 | 2.0 |
| Talc | 0 | 0 | 2.0 | 0 |

Tablets using formulation O were manufactured using direct compression. On a small scale, the tablets using formulation O were manufactured without sticking problems. However, on a larger scale, and when other batches of ladostigil tartrate with different particle size distributions were used, there were sticking problems in the tableting process.

As a result, formulations P, Q and R were manufactured using dry granulation, and using two different lubricants. This eliminated some of the sticking problems.

The stability of formulations O, P, Q and R was tested at 40° C./75% RH for 3 months, and determined by the color of the tablets at 0, 1, 2 and 3 months, which was verified by an HPLC assay of total impurities. The results are shown in Table 3:

TABLE 3

Stability Profile of Second Formulations

| Formulation | | 0 months | 1 month | 2 months | 3 months |
|---|---|---|---|---|---|
| R | Total impurities (percent) | 0.16 | 0.5 | | |
| | Appearance | Off-white | Off-white/creamy-yellow | Creamy-brown | |
| Q | Total impurities (percent) | 0.07 | | | 0.23 |
| | Appearance | White | | | Off-white |
| P | Total impurities (percent) | 0.07 | 0.3 | 0.4 | |
| | Appearance | White | Off-white/yellow | Yellow | |
| O | Total impurities (percent) | 0.07 | 0.15 | 0.23 | 0.29 |
| | Appearance | White | Off-white | Off-white | Off-white |

Formulation Q was the most stable, apparently due to the lack of sodium stearyl fumarate as a lubricant. Accordingly, optimization of double weight formulation Q was performed to increase compressibility and stability, and the results are shown in Table 4:

TABLE 4

Compressibility Profile of Third Formulations[2]

| Formulation | Compressibility[1] | Ladostigil Tartrate (mg) | Starch 1500 (mg) | SYLOID (mg) | Stearic acid (mg) | Talc (mg) |
|---|---|---|---|---|---|---|
| R1 | 2 | 64 | 40 | 5 | 3 | 4 |
| S | 1 | 64 | 40 | 5 | 3 | 8 |
| T | 5 | 64 | 40 | 5 | 6 | 4 |
| U | 5 | 64 | 40 | 5 | 6 | 8 |
| V | 1 | 64 | 40 | 5 | 3 | |
| W | 5 | 64 | 40 | 5 | 3 | |
| X | 5 | 64 | 40 | 9 | 4 | 8 |
| Y | 0.5 | 64 | 40 | 5 | 4 | 8 |
| Z | Can't press | 64 | 40 | 5 | 2 | |
| AA | 0-0.4 | 64 | 80 | 9 | 4 | 8 |
| CC | 0.2 | 64 | 80 | 5 | 4 | 8 |

[1]Compressibility was measured on a scale from 0 to 5, zero being most compressible and 5 being least compressible. The formulations graded 5 encountered severe sticking problems in the tableting process.
[2]In all formulations in Table 4, Mannitol USP was added as a filler in order to complete the tablet weight to 200 mg for each formulation.

Increasing the stearic acid levels to 8 mg/tablet (3% per tablet) increased the sticking problem. Thus, it was determined that 4 mg/tablet (2% per tablet) of stearic acid was the optimal amount.

In addition, increasing the disintegrant amount, i.e., Starch 1500, helped compressibility.

Accelerated Stability Screening

Different formulations were kept at 55° C. Stability was assessed by color changes (relative to unheated tablets) after 6 or 14 days, the results of which are shown in Table 5:

TABLE 5

Stability of Third Formulations[1]

| Formulation | Ladostigil Tartrate (mg) | Starch (mg) | SYLOID (mg) | Stearic acid (mg) | Talc (mg) | 6D | 14D |
|---|---|---|---|---|---|---|---|
| R1 | 64 | 40 | 5 | 3 | 4 | White | White |
| BB | 64 | 40 | 9 | 4 | 4 | White | White |

TABLE 5-continued

Stability of Third Formulations[1]

| For-mu-lation | Ladostigil Tartrate (mg) | Starch (mg) | SYLOID (mg) | Stearic acid (mg) | Talc (mg) | 6D | 14D |
|---|---|---|---|---|---|---|---|
| Y | 64 | 40 | 5 | 4 | 8 | White | White |
| CC | 64 | 80 | 5 | 4 | 8 | White | White to off white |
| X | 64 | 40 | 9 | 4 | 8 | White | White to off white |
| AA | 64 | 80 | 9 | 4 | 8 | White to off white | White |

[1] In the formulations of Table 5, Mannitol USP was added as a filler in order to complete the tablet weight to 200 mg for each formulation.

Formulations R1, Y, BB and CC were stable under accelerated conditions. A flow problem resulted, however, due to large variability in particle size distribution, resulting in a change in the crystallization method of ladostigil tartrate.

The manufacturing process was changed from the dry granulation process to a wet-granulation process as a result of the flow problem with the active ingredient. Water and ethanol are the two most common agents used in wet granulation. Granulation experiments were first performed with water. The appearance of the formulations containing those granulates became creamy to brownish after 1 day at 55° C., which indicated that ladostigil tartrate was unstable in the presence of water. Moreover, ladostigil tartrate was found to be incompatible with ethanol. Therefore, granulation experiments based on the CC formulation were performed with isopropanol.

Uniform, flowing granulates were obtained and tablets were compressed according to the two formulations in Table 6:

TABLE 6

Fourth Formulations

|  | A (mg) | B (mg) |
|---|---|---|
| Ladostigil Tartrate | 64.0 | 64.0 |
| Mannitol USP/BP | 35 | 35 |
| Starch 1500 | 80 | 80 |
| Pregelainized starch |  |  |
| SYLOID 244 (Silicon Dioxide) | 4.5 | — |
| Polividone 30 (PVP) | 12.5 | 12.5 |
| Stearic acid | 3 | 4 |
| Talc | 8 | 8 |

Stability tests were performed on the two formulations in 40° C./75% RH stability conditions, the results of which are shown in Tables 7 and 8:

TABLE 7

Stability of Fourth Formulations

| Batch | Time | R-CAI | CIONE | 1.17 | 2.25-2.43 | 3.39-3.41 | Total | Appearance |
|---|---|---|---|---|---|---|---|---|
| A | Zero | 0.1 | * | * | * | * | 0.1 | white |
|  | 1 month | 0.2 | * | * | * | * | 0.2 | off white |
|  | 3 months | 0.3 | 0.07 | * | 0.06 | * | 0.4 | off white |
| B | Zero | 0.08 | * | * | * | * | 0.08 | white |
|  | 1 month | 0.1 | * | 0.08 | * | * | 0.2 | white |
|  | 2 months | 0.2 | * | * | * | * | 0.2 | white |
|  | 3 months | 0.2 | * | * | * | * | 0.2 | white/off white |
|  | 4 months | 0.2 | * | * | 0.09 | * | 0.3 | white/off white |
|  | 5 months | 0.2 | * | * | * | 0.06 | 0.3 | Beige/yellow |

Relative Retention Time shown over columns 1.17, 2.25-2.43, 3.39-3.41.

*The number is listed only when the impurity peak is greater than or equal to 0.05. All units are in percent.
R-CAI and CIONE are acronyms for the following impurities: Ethyl-methyl-carbamic acid 3-amino-indan-5-yl ester and Ethyl-methyl-carbamic acid 3-oxo-indan-5-yl ester, respectively.

TABLE 8

Dissolution Profile of Fourth Formulations

| Batch No. | Time (min) | 15 | 30 | 45 |
|---|---|---|---|---|
| A | Zero | 95 | 103 | 104 |
|  | 1 month | 88 | 97 | 98 |
|  | 6 months | 94 |  | 100 |
| B | Zero |  | 96 | 96 |
|  | 1 month |  | 97 | 99 |
|  | 2 months |  | 94 | 96 |
|  | 3 months |  | 94 | 96 |
|  | 4 months |  | 94 | 96 |
|  | 5 months |  | 95 | 96 |
|  | 6 months |  | 93 | 93 |

All units are in percent.

These two formulations were found to be uniform and stable. All alternative formulations were within specifications under stress conditions (40° C./75% RH) and the color showed no change after 4 months.

More binder (PVP) was later added in order to improve structure and flowing properties after granulation.

Final formulations comprising different amounts of ladostigil tartrate are shown in Table 9:

TABLE 9

Final Formulations

| Excipient (mg) | Tablet equivalent to 20 mg Ladostigil Tartrate base | Tablet equivalent to 50 mg Ladostigil Tartrate base | Tablet equivalent to 80 mg Ladostigil Tartrate base | Function |
|---|---|---|---|---|
| Ladostigil Tartrate | 25.6 | 64.0 | 102.4 | Drug Substance |
| Mannitol USP/BP | 13.4 | 33.5 | 53.6 | Filler |
| Pregelatinized starch (starch 1500 NF) | 32.0 | 80.0 | 128.0 | Disintegrant |
| SYLOID 244 (Colloidal Silicon Dioxide) | 1.8 | 4.5 | 7.2 | Disintegrant and flowing agent |
| Polividone 30 (PVP) | 7.2 | 18.0 | 28.8 | Binder |
| Mannitol granulate | 120.0 | — | — | Filler |
| Stearic acid | 4.0 | 4.0 | 6.4 | Lubricant |
| Talc | 8.0 | 8.0 | 12.8 | Lubricant |
| Isopropyl alcohol | q.s. | q.s. | q.s. | |
| Total tablet weight | 212.0 | 212.0 | 339.2 | |

Stability tests were performed on the final formulations at 30° C./65% RH. The tablets were packaged in aluminum silver/aluminum soft blister packs.

TABLE 10

Stability of Final Formulations

| Dose (mg) | Time (months) | R-CAI | CIONE | Total Impurities |
|---|---|---|---|---|
| 20 | 0 | 0.06 | <0.05 | 0.06 |
| 20 | 12 | 0.3 | 0.07 | 0.5 |
| 50 | 0 | 0.07 | <0.02 | 0.07 |
| 50 | 12 | 0.3 | 0.08 | 0.5 |
| 80 | 0 | 0.07 | <0.05 | 0.07 |
| 80 | 12 | 0.3 | 0.08 | 0.5 |

The impurities are listed in percent by weight.

Capsules were made from the excipients in Table 9. The capsules were determined to be stable at RT for 21 months, and at 30° C. for 12 months.

Administration of Ladostigil Tartrate to Alzheimer's Disease Patients 8 patients, 7 female and 1 male, ages 62-81 with a median age of 68 and above with diagnosis of probable Alzheimer's disease according to DSM-IV (290.00 or 290.10) and NINCDS-ADRDA criteria were administered ladostigil tartrate as formulated in Table 9 according to the following schedule:

Week 1: 70 mg (50+20) once daily.

Week 2: 70 mg (50+20) twice daily.

Week 3-Week 9: 100 mg (50*2) twice daily.

4 patients (3 male and 1 female) aged 70 to 84 years old were in the placebo group.

Pharmacokinetic analysis was performed on Week 4 (maintenance analysis) and on Week 9 (termination analysis). At maintenance analysis (M), samples were collected pre-dose and at 0.25, 0.5, 1, 2, and 3 hours post-dose. At termination analysis (T), samples were collected pre-dose and at 0.25, 0.5, 1, 2, 3, 4, 6, and hours post-dose.

TABLE 11

| | Patient Number | | | | | | | |
|---|---|---|---|---|---|---|---|---|
| | 1 | 2 | 3 | 4 | 5 | 6 | 7 | 8 |
| MAO (T) (%) | −55 | −85 | −98 | −76 | −89 | −76 | −54 | −64 |
| DHPG (T) (%) | −63 | −86 | ND | ND | >−79 | −73 | −30 | −13 |
| AUC (ng * hr/mL) | | | | | | | | |
| ladostigil (M) | 314 | 589 | 1005 | 927 | 436 | 551 | 52 | 500 |
| ladostigil (T) | 246 | 2305 | 1449 | 482 | 398 | 901 | 118 | 350 |
| $C_{max}$ (nmol/mL) | | | | | | | | |
| ladostigil (M) | 1.1 | 1.2 | 3.5 | 3.9 | 1.4 | 1.5 | 0.2 | 1.7 |
| ladostigil (T) | 0.7 | 3.8 | 3.9 | 1.6 | 1.0 | 2.5 | 0.4 | 1.3 |

Mean $C_{max}$ after dosing and mean $C_{min}$ (concentration at pre-dose) of ladostigil tartrate at maintenance analysis (M) and at termination analysis (T) were determined and are listed in Table 12, as well as half life ($t_{1/2}$) at termination. The concentration measurements are expressed in nmol/ml and the $t_{1/2}$ is expressed in terms of hours.

TABLE 12

Pharmacokinetic Analysis

| Analyte | $C_{min}$ (M) | $C_{min}$ (T) | $C_{max}$ (M) | $C_{max}$ (T) | $t_{1/2}$ |
|---|---|---|---|---|---|
| Ladostigil Tartrate | 0.0164 | 0.0109 | 2.02 | 1.88 | 1.08 |

Monoamine oxidase B ("MAO-B") inhibition in plasma samples from the aforementioned patients was determined at baseline and at termination analysis using liquid scintillation counting. The percent inhibition was calculated for each patient, and the mean percent inhibition was then determined to be 75% (standard deviation=16) at the termination analysis.

Decrease of 3,4-dihydroxyphenylglycol ("DHPG") in plasma is indicative of monoamine oxidase inhibition, especially in the brain. DHPG plasma concentrations were measured in 6 of the aforementioned patients at baseline and at termination analysis, using HPLC equipped with an electrochemical detector.

The decrease in DHPG concentration in the six patients was determined. The average decrease in DHPG concentration was determined to be 57% with a standard deviation of 29.

The data show that the analytes were present at pre-dose (which corresponds to 12 hours after the previous dose) both at maintenance and at termination analyses.

There is evidence of significant MAO-B inhibition.

Cholinesterase inhibition at pre-dose administration both at maintenance and at termination analyses was also evident.

What is claimed:

1. An oral pharmaceutical composition comprising R(+)-6-(N-methyl, N-ethyl-carbamoyloxy)-N'-propargyl-1-aminoindan hemitartrate in an amount of 25 mg to 105 mg, at least one pharmaceutically acceptable excipient and up to 5% by weight of the composition of water, wherein the at least one pharmaceutically acceptable excipient is mannitol as a first filler being present in an amount of 6 to 16% by weight, mannitol granulate as a second filler being present in an amount of 0 to 56% by weight, starch as a disintegrant being present in an amount of 15 to 38% by weight, colloidal silicon dioxide as a flow agent being present in an amount of 1 to 2% by weight, and polyvinylpyrolidone as a binder being present in an amount of 3 to 8% by weight.

2. The pharmaceutical composition of claim 1, comprising 2-5% water.

3. The pharmaceutical composition of claim 1, comprising 1-3.5% water.

4. An oral pharmaceutical composition comprising R(+)-6-(N-methyl, N-ethyl-carbamoyloxy)-N'-propargyl-1-aminoindan hemitartrate in an amount of 25 mg to 105 mg, at least one pharmaceutically acceptable excipient and up to 5% by weight of the composition of water, wherein the at least one pharmaceutically acceptable excipient is mannitol as a first filler being present in an amount of 6.6% by weight, mannitol granulate as a second filler being present in an amount of 56.1% by weight, starch as a disintegrant being present in an amount of 15.2% by weight, colloidal silicon dioxide as a flow agent being present in an amount of 0.9% by weight, polyvinylpyrolidone as a binder being present in an amount of 3.4% by weight, and as a lubricant talc in an amount of 3.8% by weight and stearic acid in an amount of 1.9% by weight.

5. An oral pharmaceutical composition comprising R(+)-6-(N-methyl, N-ethyl-carbamoyloxy)-N'-propargyl-1-aminoindan hemitartrate in an amount of 25 mg to 105 mg, at least one pharmaceutically acceptable excipient and up to 5% by weight of the composition of water, wherein the at least one pharmaceutically acceptable excipient is mannitol as a first filler being present in an amount of 16.4% by weight, starch as a disintegrant being present in an amount of 37.4% by weight, colloidal silicon dioxide as a flow agent being present in an amount of 2.1% by weight, polyvinylpyrolidone as a binder being present in an amount of 8.4% by weight, and as a lubricant talc in an amount of 3.7% by weight and stearic acid in an amount of 1.9% by weight.

6. The pharmaceutical composition of claim 1 in the form of tablets, capsules, pills, powders, or granules.

7. The pharmaceutical composition of claim 6 in tablet form.

8. The pharmaceutical composition of claim 6 in capsule form.

9. A method of treating a subject afflicted with Parkinson's disease, Alzheimer's disease or dementia, or depression comprising administering to the subject a pharmaceutical composition of claim 1.

10. A method of treating a subject afflicted with Parkinson's disease, Alzheimer's disease or dementia, or depression comprising administering to the subject a pharmaceutical composition of claim 4.

11. A method of treating a subject afflicted with Parkinson's disease, Alzheimer's disease or dementia, or depression comprising administering to the subject a pharmaceutical composition of claim 5.

* * * * *